United States Patent [19]

Smith

[11] Patent Number: 5,869,650
[45] Date of Patent: Feb. 9, 1999

[54] DENDROAMIDE COMPOUNDS AND THEIR USE IN CHEMOSENSITIZING MULTIDRUG RESISTANT CELLS

[75] Inventor: Charles D. Smith, Langhorne, Pa.

[73] Assignee: Fox Chase Cancer Center, Philadelphia, Pa.

[21] Appl. No.: 669,991

[22] Filed: Jun. 21, 1996

[51] Int. Cl.$^6$ .................. C07D 498/22; C07D 513/22
[52] U.S. Cl. .................................................. 540/460
[58] Field of Search ............................................ 540/460

[56] References Cited

FOREIGN PATENT DOCUMENTS

WO9005731  5/1990  WIPO .

OTHER PUBLICATIONS

T. Tsuruo et al. Cancer Res., 41: 1967–1972 (1981).
U. de Faire et al., Eur. J. Cardiol., 6: 195–198 (1977).
J. Candell et al., Chest, 75: 200–201 (1979).
E. Aguilar et al., Tetrahedron Lett., 35: 2473–2480 (1994).
E.M. Burgess et al., J. Org. Chem., 38: 26–31 (1973).
P. Wipf et al., J. Org. Chem., 60: 7224–7229 (1995).
U. Piantini et al., J. Am. Chem. Soc., 104: 6800–6801 (1982).
N. Muller et al., J. Am. Chem. Soc., 108: 6482–6492 (1986).
A. Bax et al., J. Magn. Res., 67: 565–569 (1986).
A. Bax et al., J. Am. Chem. Soc., 108: 2093–2094 (1986).
A. Bax, J. Magn. Res., 57: 314–318 (1984).
M.P. Foster et al., J. Org. Chem., 57: 6671–6675 (1992).
A.K. Todorova et al., J. Org. Chem., 60: 7891–7895 (1995).
P. Marfey, Carlsberg Res. Commun.,49: 591–596 (1984).
I.J. Turchi et al., Chem. Rev., 75: 389–437 (1975).
N. Fusetani et al., J. Am. Chem. Soc., 113: 7811–7812 (1991).
S. Carmeli et al., Tetrahedron Lett., 34: 6681–6684 (1993).
H. Frank, J. Chromatogr. Sci., 15: 174–176 (1977).
C.R. Fairchild et al., Cancer Res., 47: 5141–5148 (1987).
E. Schneider et al., Cancer Res., 54: 152–158 (1994).
C.D. Smith et al., Oncology Res., 6: 211–218 (1994).
C.D. Smith et al., Mol. Pharm., 47: 241–247 (1995).
P. Skehan et al., J. Natl. Cancer Inst., 82: 1107–1112 (1990).
M. Prinsep et al., J. Natl. Prod., 55: 140–142 (1992).
A. Williams and R. Jacobs, Cancer Letters, 71: 97–102 (1993).
B. Degnan et al., J. Med. Chem., 32: 1349–1359 (1989).

*Primary Examiner*—Richard L. Raymond
*Attorney, Agent, or Firm*—Dann, Dorfman, Herrell and Skillman

[57] ABSTRACT

Dendroamide derivatives are disclosed which are useful in cancer therapy, especially in treating multidrug resistant cells.

3 Claims, 2 Drawing Sheets

DENDROAMIDE COMPOUNDS AND THEIR USE IN CHEMOSENSITIZING MULTIDRUG RESISTANT CELLS

This invention was made with government support under Grant CA 64983 awarded by the National Cancer Institute, Department of Health and Human Services. The government has certain rights in the invention.

FIELD OF THE INVENTION

The present invention relates to dendroamide compounds, therapeutic preparations containing such compounds and their use in cancer therapy. More particularly, this invention relates to certain dendroamide compounds and compositions possessing multidrug resistance reversing activity, and to methods of chemosensitizing multidrug resistant cells using such compounds and compositions.

BACKGROUND OF THE INVENTION

Multidrug resistance (MDR) is the term used to describe the resistance of cancer cells to chemotherapy, a resistance which can occur intrinsically or which can be acquired following a course of chemotherapy treatment. Acquired MDR occurs when tumor cells that survive initial chemotherapy are found to possess increased resistance to both the original therapeutic drug and other unrelated drugs.

Studies of acquired MDR have shown that the resistance is correlated with increased expression of cell surface glycoproteins known as P-glycoprotein and/or multidrug resistance related protein (MRP). It is believed that the mechanism of MDR involves decreased accumulation of anticancer drugs in cells due to energy-dependent transport of the drugs out of the cancer cells, which is mediated by P-glycoprotein or MRP.

Reversing agents or chemosensitizers have been discovered which reverse MDR by competing for the transport systems which are responsible for resistance. The reversing agents compete for drug binding to P-glycoprotein and/or MRP, thus effecting increased cellular accumulation of anticancer agents. Agents that reverse MDR include certain calcium channel blockers, calmodulin antagonists, alkaloid analogs, steroids and hormonal analogs, some hydrophobic cationic compounds and cyclosporins.

For example, verapamil, a calcium channel blocker, is a potent and effective reversing agent in cultured cells. Verapamil has been shown to sensitize MDR cells to anticancer drugs, promote intracellular accumulation of those drugs and compete for binding to P-glycoprotein (Tsuruo et al., Cancer Res. 41:1967 (1981)). A serious impediment to the use of verapamil and other calcium-channel blockers is the potentially life-threatening cardiovascular effects in humans at the doses required to reverse MDR (U. DeFaire and T. Lundman, J. Cardiol. 6:195 (1977); Candell et al., Chest 75:200 (1979)).

Because of their demonstrated effectiveness in attenuating drug resistance in tumor cells, the development of MDR reversing agents in anticancer chemotherapy continues to be an area of active investigation. However, a need exists for new reversing and/or chemosensitizing agents which enable treatment of drug resistant cells, so as to allow intracellular accumulation of anticancer drugs with less systemic toxicity, thereby overcoming the above-noted drawbacks attendant the use of the MDR reversing agents reported to date.

SUMMARY OF THE INVENTION

In accordance with one aspect of the present invention, compounds, sometimes referred to herein as dendroamides, are provided which potentiate the cytotoxicity of anticancer drugs and are of the formula:

in which $R_1$, $R_3$ and $R_5$ are independently selected from the group consisting of —H, —OH, —SH, —NR'R", a straight or branched, substituted or unsubstituted alkyl group having 1–6 carbon atoms, a cycloalkyl group having 4–6 carbon atoms, a cycloalkylalkyl group having 4–10 carbon atoms, or an aryl or aralkyl group having 6–10 carbon atoms, and $R_2$, $R_4$ and $R_6$ are independently selected from the group consisting of —H, —OH, —SH, —NR'R", a straight or branched, substituted or unsubstituted alkyl group having 1–6 carbon atoms, a cycloalkyl group having 4–6 carbon atoms or a cycloalkylalkyl group having 4–10 carbon atoms, said alkyl group substituents in $R_1$, $R_2$, $R_3$, $R_4$, $R_5$ and $R_6$ being selected from the group consisting of —OH, —SH, —NR'R", halogen, -O-alkyl having 1–6 carbon atoms or -S-alkyl having 1–6 carbon atoms, said R' and R" radicals being selected from the group consisting of —H and alkyl having 1–6 carbon atoms, $X_1$, $X_2$ and $X_3$ are independently selected from the group consisting of oxygen and sulfur, the dotted lines in the heterocyclic ring members indicating the presence of a single or a double bond; and the stereoisomers and pharmaceutically acceptable salts of said compounds.

According to another aspect, the present invention provides compositions comprising compounds of formula I with a biologically compatible vehicle or carrier for use in reversing MDR and/or chemosensitizing multidrug-resistant cells, as well as preventing MDR.

According to a further aspect, the present invention provides methods of using the dendroamide of formula I for prevention of MDR, as well as for reversing MDR and/or chemosensitizing multidrug-resistant cells to anti-cancer agents.

BRIEF DESCRIPTION OF THE DRAWINGS

FIGS. 2A and 2B show the chemosensitization of MCF-7/ADR breast carcinoma cells by Compound A. In FIG. 2A, MCF-7/ADR cells were treated with the indicated concentrations of Compound A in the presence of 15 μM daunomycin (□), 200 nM actinomycin D (Δ) or 4 μM cisplatin (○). In FIG. 2B, MCF-7 cells (◆) or MCF-7/ADR cells treated with 1% ethanol (◇), 0.6 (□) or 2.5 μM of Compound A (Δ) were incubated with the indicated concentrations of vinblastine.

DETAILED DESCRIPTION OF THE INVENTION

The compounds of the invention are of the general formula I, as set forth above and potentiate the cytotoxicity of anticancer drugs.

A preferred subset of compounds according to the invention have the structure of formula I wherein $R_1$, $R_3$ and $R_5$ are independently selected from the group consisting of —H, —OH, —SH, —NR'R", a straight or branched, substituted or unsubstituted alkyl group, having 1–6 carbon atoms, a cycloalkyl group having 4–6 carbon atoms or a cycloalkylalkyl group having 4–10 carbon atoms, said $R_1$, $R_3$ and $R_5$ being not all the same, and $R_2$, $R_4$ and $R_6$ are independently selected from the group consisting of —H, —OH, —SH, —NR'R", a straight or branched, substituted or unsubstituted alkyl group having 1–6 carbon atoms, a cycloalkyl group having 4–6 carbon atoms or an cycloalkylalkyl group having 4–10 carbon atoms, at least one of $R_2$, $R_4$ and $R_6$ being other than —H, said alkyl group substituents in $R_1$, $R_2$, $R_3$, $R_4$, $R_5$ and $R_6$ being selected from the group consisting of —OH, —SH, —NR'R", halogen, -O-alkyl having 1–6 carbon atoms or -S-alkyl having 1–6 carbon atoms, and said R' and R" radicals being selected from the group consisting of —H and alkyl having 1–6 carbon atoms, $X_1$, $X_2$ and $X_3$ are independently selected from the group consisting of oxygen and sulfur, the dotted line in the heterocyclic ring members indicating the presence of a single or double bond, and the stereoisomers and pharmaceutically acceptable salts thereof. Especially preferred are compounds of formula I, in which $X_1$ and $X_2$ are S, $X_3$ is O and $R_1$, $R_2$, $R_3$, $R_4$, $R_5$, $R_6$ are selected from the group consisting of H and a straight or branched alkyl having 1–4 carbon atoms.

Most preferred is a compound (hereinafter referred to as Compound A) having the formula:

In the chemical structure immediately above, the dashed wedge represents a bond which projects below the plane of the molecule (away from the viewer); and the straight lines represent bonds which lie in the plane of the molecule.

The compounds of the invention can be categorized as cyclic hexapeptide derivatives in which serine or threonine and cysteine residues have been condensed to form the oxazole and thiazole rings, respectively. The total synthesis of a compound of this type (known as bistratamide C) has been recently described by E. Aguilar and A. I. Meyers in *Tetrahedron Lett.* 35:2477–2480 (1994). Synthesis of dendroamide analogues may follow a similar approach according to the general synthetic scheme shown below.

* t-Butoxycarbonyl
** Dicyclohexylcarbodiimide
*** Tetrahydrofuran
+ Dimethyl ether
++ Trifluoroacetic acid The above-described synthetic scheme can be used to synthesize the following representative cyclic hexapeptide compounds in which the standard amino acids are represented by the accepted three letter abbreviations:

A. Compounds containing oxazole (Oxz), oxazoline (Ozl) or methyloxazoline (mOzl)
cyclo-Ala -Oxz- Ala -Oxz- Ala -Oxz
cyclo-Ala -Ozl- Ala -Ozl- Ala -Ozl
cyclo-Ala -mOzl- Ala -mOzl- Ala -mOzl
cyclo-Arg -Oxz- Arg -Oxz- Arg -Oxz
cyclo-Arg -Ozl- Arg -Ozl- Arg -Ozl
cyclo-Arg -mOzl- Arg -mOzl- Arg -mOzl
cyclo-Asn -Oxz- Asn -Oxz- Asn -Oxz
cyclo-Asn -Ozl- Asn -Ozl- Asn -Ozl
cyclo-Asn -mOzl- Asn -mOzl- Asn -mOzl
cyclo-Asp -Oxz- Asp -Oxz- Asp -Oxz
cyclo-Asp -Ozl- Asp -Ozl- Asp -Ozl
cyclo-Asp -mOzl- Asp -mOzl- Asp -mOzl
cyclo-Cys -Oxz- Cys -Oxz- Cys -Oxz
cyclo-Cys -Ozl- Cys -Ozl- Cys -Ozl
cyclo-Cys -mozl- Cys -mOzl- Cys -mOzl
cyclo-Gln -Oxz- Gln -Oxz- Gln -Oxz
cyclo-Gln -Ozl- Gln -Ozl- Gln -Ozl
cyclo-Gln -mozl- Gln -mOzl- Gln -mOzl
cyclo-Glu -Oxz- Glu -Oxz- Glu -Oxz
cyclo-Glu -Ozl- Glu -Ozl- Glu -Ozl
cyclo-Glu -mOzl- Glu -mOzl- Glu -mOzl
cyclo-Gly -Oxz- Gly -Oxz- Gly -Oxz
cyclo-Gly -Ozl- Gly -Ozl- Gly -Ozl
cyclo-Gly -mOzl- Gly -mOzl- Gly -mOzl
cyclo-His -Oxz- His -Oxz- His -Oxz
cyclo-His -Ozl- His -Ozl- His -Ozl cyclo-His -mOzl- His -mOzl- His -mOzl
cyclo-Ile -Oxz- Ile -Oxz- Ile -Oxz
cyclo-Ile -Ozl- Ile -Ozl- Ile -Ozl
cyclo-Ile -mOzl- Ile -mozl- Ile -mOzl
cyclo-Leu -Oxz- Leu -Oxz- Leu -Oxz
cyclo-Leu -Ozl- Leu -Ozl- Leu -Ozl
cyclo-Leu -mOzl- Leu -mOzl- Leu -mozl
cyclo-Lys -Oxz- Lys -Oxz- Lys -Oxz
cyclo-Lys -Ozl- Lys -Ozl- Lys -Ozl
cyclo-Lys -mOzl- Lys -mOzl- Lys -mOzl
cyclo-Met -Oxz- Met -Oxz- Met -Oxz
cyclo-Met -Ozl- Met -Ozl- Met -Ozl
cyclo-Met -mozl- Met -mOzl- Met -mOzl
cyclo-Phe -Oxz- Phe -Oxz- Phe -Oxz
cyclo-Phe -Ozl- Phe -Ozl- Phe -Ozl
cyclo-Phe -mozl- Phe -mozl- Phe -mozl
cyclo-Ser -Oxz- Ser -Oxz- Ser -Oxz
cyclo-Ser -Ozl- Ser -Ozl- Ser -Ozl
cyclo-Ser -mOzl- Ser -mOzl- Ser -mozl
cyclo-Thr -Oxz- Thr -Oxz- Thr -Oxz
cyclo-Thr -Ozl- Thr -Ozl- Thr -Ozl
cyclo-Thr -mOzl- Thr -mOzl- Thr -mozl
cyclo-Trp -Oxz- Trp -Oxz- Trp -Oxz
cyclo-Trp -Ozl- Trp -Ozl- Trp -Ozl
cyclo-Trp -mOzl- Trp -mOzl- Trp -mOzl
cyclo-Tyr -Oxz- Tyr -Oxz- Tyr -Oxz
cyclo-Tyr -Ozl- Tyr -Ozl- Tyr -Ozl
cyclo-Tyr -mOzl- Tyr -mOzl- Tyr -mOzl
cyclo-Val -Oxz- Val -Oxz- Val -Oxz
cyclo-Val- Ozl- Val -Ozl- Val -Ozl
cyclo-Val -mozl- Val -mOzl- Val -mOzl B. Compounds containing thiazole (Thz), thiazoline (Tzl) or methylthiazoline (mTzl)

cyclo-Ala -Thz- Ala -Thz- Ala -Thz
cyclo-Ala -Tzl- Ala -Tzl- Ala -Tzl
cyclo-Ala -mTzl- Ala -mTzl- Ala -mTzl
cyclo-Arg -Thz- Arg -Thz- Arg -Thz
cyclo-Arg -Tzl- Arg -Tzl- Arg -Tzl
cyclo-Arg -mTzl- Arg -mTzl- Arg -mTzl
cyclo-Asn -Thz- Asn -Thz- Asn -Thz
cyclo-Asn -Tzl- Asn -Tzl- Asn -Tzl
cyclo-Asn -mTzl- Asn -mTzl- Asn -mTzl
cyclo-Asp -Thz- Asp -Thz- Asp -Thz
cyclo-Asp -Tzl- Asp -Tzl- Asp -Tzl
cyclo-Asp -mtzl- Asp -mTzl- Asp -mTzl
cyclo-Cys -Thz- Cys -Thz- Cys -Thz
cyclo-Cys -Tzl- Cys -Tzl- Cys -Tzl
cyclo-Cys -mTzl- Cys -mTzl- Cys -mTzl
cyclo-Gln -Thz- Gln -Thz- Gln -Thz
cyclo-Gln -Tzl- Gln -Tzl- Gln -Tzl
cyclo-Gln -mTzl- Gln -mTzl- Gln -mTzl
cyclo-Glu -Thz- Glu -Thz- Glu -Thz
cyclo-Glu -Tzl- Glu -Tzl- Glu -Tzl
cyclo-Glu -mTzl- Glu -mTzl- Glu -mTzl
cyclo-Gly -Thz- Gly -Thz- Gly -Thz
cyclo-Gly -Tzl- Gly -Tzl- Gly -Tzl
cyclo-Gly -mTzl- Gly -mTzl- Gly -mTzl
cyclo-His -Thz- His -Thz- His -Thz
cyclo-His -Tzl- His -Tzl- His -Tzl
cyclo-His -mTzl- His -mTzl- His -mTzl
cyclo-Ile -Thz- Ile -Thz- Ile -Thz
cyclo-Ile -Tzl- Ile -Tzl- Ile -Tzl
cyclo-Ile -mTzl- Ile -mTzl- Ile -mtzl
cyclo-Leu -Thz- Leu -Thz- Leu -Thz
cyclo-Leu -Tzl- Leu -Tzl- Leu -Tzl
cyclo-Leu -mTzl- Leu -mTzl- Leu -mTzl
cyclo-Lys -Thz- Lys -Thz- Lys -Thz
cyclo-Lys -Tzl- Lys -Tzl- Lys -Tzl
cyclo-Lys -mTzl- Lys -mTzl- Lys -mTzl
cyclo-Met -Thz- Met -Thz- Met -Thz
cyclo-Met -Tzl- Met -Tzl- Met -Tzl
cyclo-Met -mTzl- Met -mTzl- Met -mTzl
cyclo-Phe -Thz- Phe -Thz- Phe -Thz
cyclo-Phe -Tzl- Phe -Tzl- Phe -Tzl
cyclo-Phe -mTzl- Phe -mTzl- Phe -mTzl
cyclo-Ser -Thz- Ser -Thz- Ser -Thz
cyclo-Ser -Tzl- Ser -Tzl- Ser -Tzl
cyclo-Ser -mTzl- Ser -mTzl- Ser -mTzl
cyclo-Thr -Thz- Thr -Thz- Thr -Thz
cyclo-Thr -Tzl- Thr -Tzl- Thr -Tzl
cyclo-Thr -mTzl- Thr -mTzl- Thr -mTzl
cyclo-Trp -Thz- Trp -Thz- Trp -Thz
cyclo-Trp -Tzl- Trp -Tzl- Trp -Tzl
cyclo-Trp -mTzl- Trp -mTzl- Trp -mTzl
cyclo-Tyr -Thz- Tyr -Thz- Tyr -Thz
cyclo-Tyr -Tzl- Tyr -Tzl- Tyr -Tzl
cyclo-Tyr -mTzl- Tyr -mTzl- Tyr -mTzl
cyclo-Val -Thz- Val -Thz- Val -Thz
cyclo-Val -Tzl- Val -Tzl- Val -Tzl
cyclo-Val -mTzl- Val -mTzl- Val -mTzl.

Numerous other cyclic hexapeptides can also be synthesized, according to the above-described synthetic scheme, using various combinations of naturally occurring amino acids, non-naturally occurring amino acids or synthetically prepared amino acids together with the six heterocyclic moieties listed above.

As shown in the foregoing reaction scheme, the compounds of the invention may be assembled from three protected dipeptide derivatives. For precursors containing oxazoline or oxazole groups, the starting materials are dipeptides consisting of tBOC-amino acid-serine-methyl ester or tBOC-amino acid-threonine-methyl ester, where "amino acid" represents any essential, naturally occurring or non-naturally occurring amino acid, except proline (which will not support cyclization of the final product). The R-groups of the final product derive from the side-chain of the starting amino acid. Dipeptides with serine or threonine are treated with Burgess Reagent (E. M. Burgess et al., *J. Org. Chem.* 38:26 (1973)) to generate the corresponding oxazoline, which is subsequently oxidized by $NiO_2$ to generate oxazole-containing compounds. Aguilar and Meyers, supra, reported yields of 60–78% and 22–53% for these two reactions, respectively, with preservation of the stereochemistry of the chiral carbon. The amino groups of these compounds are then deprotected to give amino oxazoles.

Two approaches toward the synthesis of the thiazole-containing precursors have been identified. In the procedure of Aguilar and Meyers, supra, as shown in the synthetic scheme above, a modified Hantzsch reaction is used to prepare thiazole aminoesters from α-aminothioamides, in which $R_1$, $R_3$ and $R_5$ can be aliphatic or aromatic (E. Aguilar and A. I. Meyers, *Tetrahedron Lett.* 35:2473–2476 (1994)). Deprotection of the ethyl ester results in the free acid for coupling.

A second approach to the preparation of the thiazole intermediates was described by P. Wipf and S. Venkatraman in *J. Org. Chem.* 60:7224–7229 (1995). By this procedure, oxazolines (as prepared above) are converted to α-methyl cysteine derivatives by treatment with thioacetic acid. Aminolysis and simultaneous cyclodehydration by titanium tetrachloride produces a thiazoline compound which can be oxidized with benzeneselenic acid to the corresponding thiazole. The final cyclic dendroamide products are then prepared by coupling various combinations of oxazoles, oxazolines, thiazoles and thiazolines using standard peptide linking methodologies and cyclization of the hexapeptide analogue. Final closure of bistratamide C was accomplished by refluxing in toluene, or by deprotection and treatment with diphenylphosphorylazide and spontaneous cyclization (E. Aguilar and A. I. Meyers, *Tetrahedron Lett.* 35:2477–2480 (1994)).

Compound A of this invention may be synthesized from tBOC-alanine-threonine-methyl ester, 2-tBOC-aminothiopropylamide, and 2-tBOC-aminothioisopentylamide using the Aguilar and Meyers approach and/or from tBOC-alanine-threonine-methyl ester, tBOC-alanine-serine-methyl ester and tBOC-valine-threonine-methyl ester by the Wipf and Venkatraman approach. Importantly, it is apparent that a large number of compounds can be synthesized by combination of different serine- or threonine-derived oxazole or thiazole precursors. These include examples where the $R_1$, $R_2$, $R_3$, $R_4$, $R_5$ and $R_6$ groups are derived from the side chains of standard, naturally-occurring or other non-naturally occurring or synthetically prepared amino acids by starting with protected dipeptides containing serine or threonine or analogues of threonine.

The gross structure and relative stereochemistry of the dendroamides of the invention were elucidated by spectral analysis. The absolute stereochemistry of compound A was determined by Marfey and chiral GC/MS analyses of derivatives formed from acid hydrolysis of the intact and ozonized compound. The structural characterization of the compounds of the invention can be carried out in the manner exemplified below.

Biological studies of Compound A as an MDR reversing agent have been performed. MDR reversal by means of chemosensitizing cells to anticancer drugs was measured using the potentiation of cytotoxicity by anticancer drugs in the presence of Compound A. Compound A-promoted accumulation of $^3$H-labelled anticancer drugs in MDR cells was also studied. Finally, MDR inhibition due to antagonistic binding of Compound A to p-glycoprotein was measured as the reduction in photoaffinity labelling of p-glycoprotein by substrates. Chemosensitizing activity can be determined according to potentiation of cytotoxicity of anticancer drugs in the presence of Compound A as exemplified below.

The results of biological studies of Compound A as a MDR reversing agent are described below.

As previously noted, the compounds of formula I, above, including their stereoisomers and pharmaceutically acceptable salts, exhibit chemosensitizing activity against multidrug-resistant cells. The compounds of the invention can be administered, for example, in the form of a chloride salt.

The pharmaceutically acceptable salts of the compound of formulas I are prepared following procedures which are familiar to those skilled in the art.

The chemosensitizing pharmaceutical compositions of the present invention comprise one or more of the compounds of formula I, above, as the active ingredient in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Fifteenth Edition, E. W. Martin (Mack Publishing Co., Easton, Pa., 1975) discloses various vehicles or carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 1% and not more than 95% by weight based on the total weight of the composition, including carrier medium and/or auxiliary agent(s). Preferably, the proportion of active agent varies between 2% to 70% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known excipients or diluents for medicaments may all be suitable as carrier media.

The compounds of the invention may be administered using any amount and any route of administration effective for chemosensitizing multidrug-resistant cells. Thus, the expression "therapeutically effective amount", as used herein, refers to a nontoxic but sufficient amount of the chemosensitizing agent to provide the desired effect against multidrug resistant cells. The exact amount required will vary from subject to subject, depending on the species, age, and general condition of the subject, the particular chemosensitizing agent, its mode of administration, and the like.

The chemosensitizing compounds of the invention are preferably formulated in dosage unit form for ease of administration and uniformity of dosage. "Dosage unit form" as used herein refers to a physically discrete unit of chemosensitizing agent appropriate for the patient to be treated. Each dosage should contain the quantity of active material calculated to produce the desired therapeutic effect either as such, or in association with the selected pharmaceutical carrier medium. Typically, the chemosensitizing compound of the invention will be administered in dosage units containing from about 0.1 mg to about 100,000 mg of the agent, with a range of about 1 mg to about 5000 mg being preferred.

The compounds of the invention may be administered orally, parenterally, such as by intramuscular injection, intraperitoneal injection, intravenous infusion or the like. The compounds of the invention may be administered orally or parenterally at dosage levels of about 0.001 to about 1000 mg/kg and preferably from about 0.01 to about 50 mg/kg, of patient body weight per day, one or more times a day, to obtain the desired therapeutic effect.

Although the compounds described herein can be administered to any subject which is susceptible to development of multidrug resistance, the compounds are intended particularly for the treatment of cancer in humans.

The compounds of the invention will typically be administered from 1 to 4 times a day so as to deliver the above-mentioned daily dosage. Alternatively, dosages within these ranges can be administered by constant infusion over an extended period of time, usually 3 to 96 hours, until the desired therapeutic benefits have been obtained. However, the exact regimen for administration of the compounds and compositions described herein will necessarily be dependent on the needs of the individual patient being treated, the type of treatment administered and the judgment of the attending physician.

The compounds of the invention can be used in various protocols for treating cancer patients. For example, the compounds of the invention can be used in a method for treating tumor cells in a patient requiring such treatment. This method would comprise administering to a cancer patient a compound of formula I in an amount effective to attenuate drug resistance in said cells. The compounds of the invention can also be used in a method for treating hyperproliferative cells in a patient requiring such treatment. This method would comprise administering to a cancer patient a compound of formula I in an amount effective to inhibit the proliferation of said cells.

The compounds of the invention can further be used in a method for potentiating an anticancer drug in a cancer patient undergoing chemotherapy. This method would comprise administering an anticancer drug and also administering to the patient a compound of formula I, above, in an amount effective to enhance the therapeutic efficacy of the anticancer drug. In this method, the compound of formula I may be administered to potentiate a natural product anticancer drug, an antitumor antibiotic anticancer drug, a natural or synthetic analogue of an antitumor agent, an antimitotic agent anticancer drug, or a natural or synthetic analogue of an antimitotic agent. The antitumor antibiotic or the natural or synthetic analogue of an antitumor agent may be selected from the group consisting of daunorubicin, doxorubicin, idarubicin, mitoxanthrone, dactinomycin, bleomycin and plicamycin. The antimitotic agent or the natural or synthetic analogue of an antimitotic agent may be selected from the group consisting of topoisomerase inhibitors, microtubule inhibitors, etoposide, teniposide, amsacrine, topotecan, camptothecin, vinblastine, vincristine, vindesine, colchicine, paclitaxel, taxotere or other such agents that are subject to MDR. In this method, the compound of formula I, above, can also be administered in combination with an additional compound effective to sensitize drug resistant tumor cells, the amount of the combination being effective to enhance the therapeutic efficacy of the anticancer drug. The additional compound may be selected from the group consisting of dihydropyridines, thioxanthenes, phenothiazines, cyclosporines, acridonecarboxamides, verapamil, cyclosporin A, PSC 833, tamoxifen, quinidine, bepridil, ketoconazole, megestrol acetate and estramustine.

In view of the beneficial effect on reversal of MDR produced by the compounds of the invention, it is anticipated that these compounds will be useful not only for therapeutic treatment after the onset of MDR, but also for MDR prevention in patients about to undergo chemotherapy for the first time. The above-noted dosages will be essentially the same whether for treatment or prevention of MDR.

The following examples are provided to describe the invention in further detail. These examples, which set forth the best mode presently contemplated for carrying out the invention, are intended to illustrate and not to limit the invention.

Examples 1–2 describe the purification and structural characterization of Compound A of the present invention.

EXAMPLE 1

Structural Elucidation of Compound A

The specific rotation of Compound A is $[\alpha]_D=+40.5°$ measured in $CH_2Cl_2$ (c 3.50). The ultraviolet absorption spectrum of Compound A in MeOH is characterized by a maximum absorption at $\lambda=224$ nm with an extinction coefficient of $\epsilon=28000$. The infrared spectrum of a neat sample of Compound A shows intense absorptions at 3396 $cm^{-1}$ which is characteristic of the NH stretching vibration of a secondary amide, 1668 $cm^{-1}$ which is characteristic of an amide-I band, and 1538 $cm^{-1}$ which is characteristic of an amide-II band.

The results of high resolution electron impact mass spectroscopy (EIMS) obtained in the EI mode show that Compound A has the molecular formula $C_{21}H_{24}N_6O_4S_2$ based on high resolution mass measurement of the molecular ion with m/z=488.1342 (relative intensity=7.6 and error=−4.2 mmu). The EIMS spectrum also shows a large M-43 fragment ion due to the loss of $C_3H_7$ with the molecular formula $C_{18}H_{17}N_6O_4S_2$ and m/z=445.0690 (relative intensity=100 and error=+6.3 mmu). Important fragment ions that are consistent with the thiazole- and methyloxazole-containing residues present in Compound A were also observed. The structures, m/z ratios and relative intensities of those fragment ions are given below.

NMR spectra were obtained using an 11.75-T instrument operating at 500 MHz for $^1H$ and 125 MHz for $^{13}C$. $^1H$ chemical shifts are referenced to residual $CHDCl_2$ (5.32 ppm) in $CD_2Cl_2$. $^{13}C$ chemical shifts are referenced to the solvent ($CD_2Cl_2$, 52.8 ppm). All $^1H$ and $^{13}C$ assignments are based on detailed COSY (U. Piantini et al., *J. Am. Chem. Soc.* 104:6800–6801 (1982); N. Muller et al., *J. Am. Chem. Soc.* 106:6482–6492 (1986)), HMQC, and HMBC analyses where one bond $^1H$-$^{13}C$ connectivities have been determined by HMQC (A. Bax and S. Subramanian, *J. Magn. Res.* 67:5659 (1986)) and two and three bond (also four bond) $^1H$-$^{13}C$ connectivities have been determined by HMBC (A. Bax and M. F. Summers, *J. Am. Chem. Soc.* 108:2093–2094 (1986)). Some of the important $^1H$-$^{13}C$ correlations, viz. the ones deciding the sequence of the peptide, were supported by selective INEPT experiments (A. Bax, *J. Magn. Res.* 57:314–318 (1984)).

The $^1H$ and $^{13}C$-NMR spectral data for Compound A are given in Table 1. The observed chemical shift data are in good agreement with values reported for the two thiazole amino acid units (Val-Tzl and Ala-Tzl) in bistratamide C (M. P. Foster et al., *J. Org. Chem.* 57:6671–6675 (1991)) and the methyloxazole amino acid unit (Ala-mOzl) in nostocyclamide (A. K. Todorova et al., *J. Org. Chem.* 60:7891–7895 (1995)). $^1H$-$^{13}C$ correlations from HMBC and selective INEPT experiments, viz. H9-C8, H13-C14 and H1-C21, allowed sequencing of the three amino acid units into a total gross structure of Compound A.

TABLE 1

NMR Data for Compound A
(Cyclo-D-Val-Tzl-D-Ala-Tzl-D-Ala-mOzl)

| C or N Position | $\delta(^{13}C)$ | $\delta(^{1}H)$ (mult,$J_{HH}$Hz) | $^{1}H$-$^{1}HCOSY$ | HMBC[a] |
|---|---|---|---|---|
| N1 | | 8.44 (br d; 8.2) | 1 | 21, 1, 5 |
| 1 | 56.1 | 5.31 (dd; 8.2, 4.8) | N1H, 2 | 21, 2, 3, 4, 5 |
| 2 | 35.6 | 2.28 (d of septet; 4.8; 6.9) | 1, 3, 4 | 1, 3, 4, 5 |
| 3 | 18.3 | 1.02 (d; 6.9) | 2 | 1, 2, 4 |
| 4 | 18.5 | 9.95 (d; 6.9) | 2 | 1, 2, 3 |
| 5 | 168.9 | | | |
| 6 | 149.2 | | | |
| 7 | 124.0 | 8.11 (s) | | 5, 6, 8[b] |
| 8 | 159.7 | | | |
| N3 | | 8.52 (br d; 8.2) | 9 | 8, 9, 11 |
| 9 | 47.3 | 5.69 (dq; 8.2, 6.8) | N3H, 10 | 8, 10, 11 |
| 10 | 25.1 | 1.68 (d; 6.8) | 9 | 9, 11 |
| 11 | 171.7 | | | |
| 12 | 149.2 | | | |
| 13 | 123.8 | 8.09 (s) | | 11, 12, 14[b] |
| 14 | 160.0 | | | |
| N5 | | 8.61 (br d; 6.6) | 15 | 14, 15, 17 |
| 15 | 44.6 | 5.17 (br quintet; 6.6) | N5H, 16 | 14, 16, 17 |
| 16 | 21.1 | 1.65 (d; 6.6) | 15 | 15, 17 |
| 17 | 162.1 | | | |
| 18 | 154.0 | | | |
| 19 | 128.8 | | | |
| 20 | 11.7 | 2.63 (s) | | 18, 19, 21 |
| 21 | 160.7 | | | |

[a]Carbon correlations./[b]Determined by selective INEPT experiment.

EXAMPLE 2

Determination of Absolute Stereochemistry of Compound A

To determine the absolute configuration of the methyloxazole amino acid unit (Ala-mOzl), Compound A was subjected to vigorous acid hydrolysis and the acid hydrolyzate was analyzed by the Marfey method (P. Marfey, *Carlsberg Res. Commun.* 49:591–596 (1984)).

(a) Direct Acid Hydrolysis: Compound A (1.0 mg) in 0.3 mL of 6N HCl was heated in a reaction vial at 110° C. for 16 hours. The solvent was removed under vacuum and the dried acid hydrolyzate was derivatized and subjected to Marfey analysis.

(b) Marfey Analysis: Dried acid hydrolyzate described above (0.3–1.0 mg) in 100 μL of water was treated successively with 1 mg of sodium (5-fluoro-2,4-dinitrophenyl)-L-alaninamide (FDAA, Marfey reagent) in 200 μL of acetone followed by 40 μL of 1N sodium bicarbonate solution and the mixture was heated at 45° C. for 1 hour. After cooling to room temperature, 20 μL of 2N HCl was added and the resulting solution was analyzed by reverse-phase HPLC on a 250×4.6 mm C18 column (ALTEX ultrasphere 5μ) using a linear gradient of 10 to 50% MeCN in 0.05M Et$_3$N/ phosphate buffer at pH 3 over 45 minutes (isocratic conditions thereafter) at a flow rate of 1 mL/min. Standards were prepared using the same procedure by treating each authentic amino acid. Only the oxazole ring was cleaved by direct acid hydrolysis to generate D-alanine from Compound A. (I. J. Turchi and M. J. S. Dewer, *Chem. Rev.* 75:389–437 (1984); N. Fusetani et al., *J. Am. Chem. Soc.* 113:7811–7812 (1975); S. Carmeli et al., *Tetradehron Lett.* 34:6681–6684 (1993)) Therefore, the configuration of C-15 in Compound A was R. Furthermore, comparison of the retention times and coinjection experiments of the FDAA derivatized direct hydrolyzates, ozonized hydrolyzates and similarly derivatized authentic amino acids established that all amino acid residues in Compound A have the D-configuration.

To determine the absolute configuration of the thiazole amino acids, the peptides were first ozonized and then subjected to vigorous acid hydrolysis followed by Marfey and GC/MS (H. Frank, *J. Chromatogr. Sci.* 15:174–176 (1977)) analyses. ozonolysis results in cleavage of both the oxazole and thiazole rings.

(a') Ozonolysis and Acid Hydrolysis: A stream of O$_3$ was bubbled through a solution of Compound A (1.0 mg) in 10 mL of CH$_2$Cl$_2$ at 25° C. for 10 minutes. The solvent was removed under a stream of N$_2$ and the residue was dissolved in 0.3 mL of 6N HCl and heated at 110° C. for 24 hours. After removal of the solvent, the residue was derivatized and subjected to Marfey and chiral GC/MS analyses.

(b') Chiral GC/MS Analysis: A mixture of the dried hydrolyzate described above in 0.3 mL of isopropanol and 0.05 mL of acetyl chloride was heated at 100° C. for 45 minutes. The excess reagent was then evaporated at 115° C. under a stream of nitrogen and the residue, which contained the isopropyl esters of the various amino acids, was treated with 0.5 mL of 1:1 (CF$_3$CF$_2$CO)$_2$O/CH$_2$Cl$_2$ at 100° C. for 15 minutes. After cooling to room temperature, the excess reagent was evaporated with a stream of dry nitrogen and the resulting mixture of isopropyl esters of N-pentafluoropropyl amino acids was dissolved in 0.5 mL of CH$_2$Cl$_2$ for GCMS analysis on a 25 m×0.25 mm Chirasil-Val column (Alltech). The following conditions were used for the GC: a 12 psi head pressure (flow rate estimated to be about 0.6 mL/sec) and a column temperature held at 35° C. for 4 minutes after injection of the sample and then increased from 35° C. to 100° C. at 2.0°/min, and finally increased from 100° C. to 195° C. at 6.0° C./min and held 12.0 minutes. The same procedure was repeated for standard samples of authentic amino acid. By comparison of the retention times and mass spectra of the derivatized hydrolyzates and authentic amino acids, D-alanine and D-valine were detected in the hydrolyzate of ozonized Compound A. Therefore, all of the chiral carbons in Compound A were R.

Examples 3–6 set forth the results of biological testing of Compound A of the invention for MDR reversal activity.

EXAMPLE 3

Effects of Compound A and Verapamil on Drug Accumulation in Breast Carcinoma Cells The reduction in intracellular accumulation of anticancer drugs due to expression of P-glycoprotein can be at least partially reversed by compounds which interact with the drug transporter. This example shows the effect of Compound A on [$^3$H]vinblastine accumulation in breast carcinoma cells.

MCF-7 breast carcinoma cells and MCF-7/ADR cells, an MDR subline which overexpresses P-glycoprotein (C. R. Fairchild et al., *Cancer Res.* 47:5141–5148 (1987), were obtained from the Division of Cancer Treatment at the National Cancer Institute. MCF-7/VP cells, which express multidrug resistance-related protein (MRP) but not P-glycoprotein, were provided by Drs. Schneider and Cowan. (E. Schneider et al., *Cancer Res.* 54:152–158 (1994). The effects of Compound A and verapamil on intracellular accumulation of [$^3$H]vinblastine were determined as described in C. D. Smith et al., *Oncology Res.* 6:211–218 (1994) and C. D. Smith et al., *Mol. Pharm.* 45:241–247 (1995), using 20 nm [$^3$H]vinblastine sulfate (10–15 Ci/mmole) from the Amersham Corporation.

Figure 1:
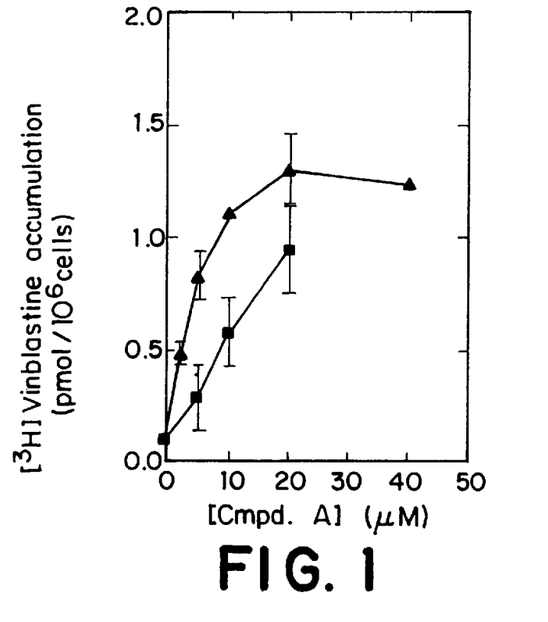
FIG. 1 shows the effect of a preferred compound of the invention (Compound A) on [$^3$H]vinblastine accumulation by MCF-7/ADR breast carcinoma cells. Cells were incubated with the indicated concentrations of Compound A (▲) or verapamil (■).

The results of the study showing the effects of Compound A and verapamil on [$^3$H]vinblastine accumulation in MCF-7/ADR cells are given in FIG. 1. Cells were incubated with the indicated concentrations of Compound A (▲) or verapamil (■) for 30 minutes. [$^3$H]vinblastine was then added and its intracellular accumulation after 60 minutes was determined. Values shown in FIG. 1 represent the mean ± standard deviation accumulation of [$^3$H]vinblastine in triplicate samples in one of three similar experiments.

FIG. 1 shows that Compound A was more potent than verapamil in its ability to increase the accumulation of [$^3$H]vinblastine in MCF-7/ADR cells. Compound A reached 750% of control at 5 μM and maximal effect at 20 μM. Neither Compound A nor verapamil increased the accumulation of [$^3$H]vinblastine in MCF-7 cells which shows that Compound A and verapamil reverse the inhibition of drug transport by P-glycoprotein.

This experiment demonstrated that the accumulation of [$^3$H]vinblastine in the MCF-7/ADR cell line which overexpress P-glycoprotein was strongly enhanced by Compound A of the invention.

EXAMPLE 4

Chemosensitization of MDR Breast Carcinoma Cells by Compound A and Verapamil

The ability of Compound A to reverse MDR was examined using MCF-7/ADR cells breast carcinoma cells which were obtained as described in Example 5. The effects of Compound A on cell growth were characterized using the sulforhodamine binding assay (P. Skehan et al., *J. Natl. Cancer Inst.* 82:1107–1112 (1990)) as described in C. D. Smith et al., *Oncology Res.* 6:211–218 (1994) and C. D. Smith et al., *Mol. Pharm.* 45:241–247 (1995). Cell survival was assessed after 48 hours of treatment and was expressed as the percentage of cells killed.

Figure 2A:
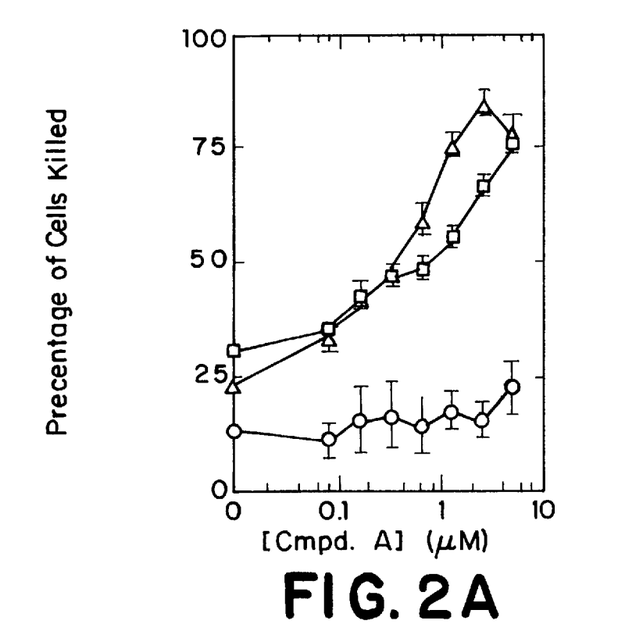
Figure 2B:
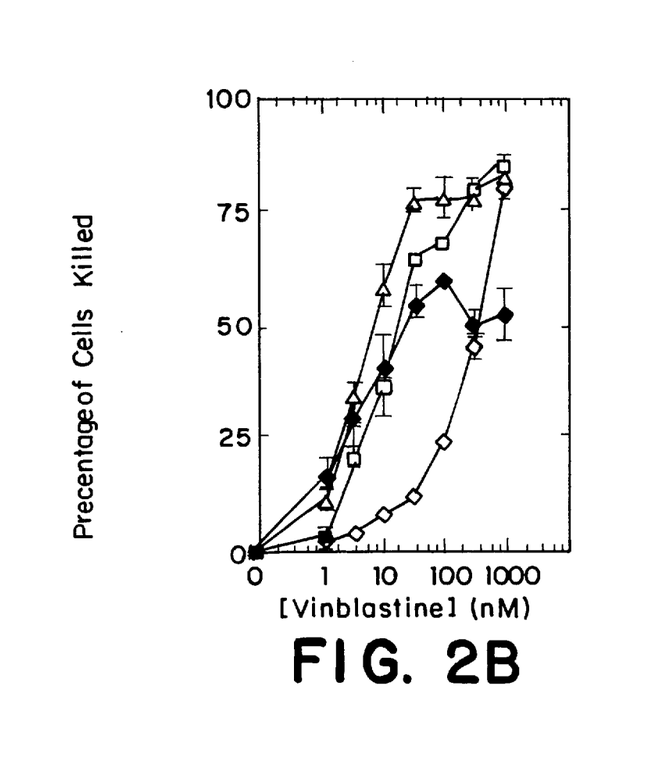

The results of the chemosensitization tests showing the effect of the MDR reversing agent Compound A on cell killing by anticancer drugs in the multiple drug resistant MCF-7/ADR cells are shown in FIGS. 2A and 2B. The MCF-7/ADR cells were treated with the indicated concentrations of Compound A in the presence of daunomycin, actinomycin D and or cisplatin. Values shown in FIGS. 2A and 2B represent the mean±standard deviation for triplicate samples in one of two similar experiments.

FIG. 2A shows that the cells were killed more effectively by combinations of daunomycin or actinomycin D with Compound A, as compared with identical doses of daunomycin or actinomycin D alone. Dose-response curves for this activity were very similar to those for intracellular drug accumulation, demonstrating activity at submicromolar concentrations. In contrast, Compound A did not alter the cytotoxicity of cisplatin, which is not a substrate for P-glycoprotein.

FIG. 2B shows that Compound A concentrations of 0.6 μM or greater increased the sensitivity of MCF-7/ADR cells to vinblastine to the level of sensitivity observed for parental MCF-7 cells. The results given in FIG. 2B show that Compound A completely overcomes P-glycoprotein-mediated MDR in this model system.

This experiment demonstrated that Compound A reversed the multiple drug resistance of the breast carcinoma MCF-7/ADR cell line by markedly potentiating cell killing by the anticancer drug daunomycin, actinomycin D and vinblastine.

EXAMPLE 5

Photoaffinity Labeling of P-glycoprotein in Breast Cancer Cells by Compound A

The binding of a compound to P-glycoprotein can be inferred if it reduces photoaffinity labeling by substrates such [$^3$H]azidopine. Increasing concentrations of Compound A or verapamil caused progressive decreases in binding of [$^3$H]azidopine to P-glycoprotein in membranes from MCF-7/ADR cells. Photolabeling of P-glycoprotein was reduced by 50% by 0.5 and 10 μM of Compound A and verapamil, respectively. Reduction of photoaffinity labeling of P-glycoprotein by [$^3$H]azidopine in the presence of Compound A strongly indicates direct binding of Compound A to P-glycoprotein.

This experiment shows that Compound A reversed the multi-drug resistance of in MCF-7/ADR cells by directly binding with P-glycoprotein.

EXAMPLE 6

Chemosensitization of MRP Breast Carcinoma Cells by Compound A and Verapamil

Reversal of multidrug resistance-related protein-mediated drug resistance (MRP) is defined as the ability of the compound to potentiate the cytotoxicity of MRP-transported drugs in cells which express multidrug resistance-related protein. The ability of Compound A to reverse MRP-mediated drug resistance was examined using MCF-7/VP breast carcinoma cells which express multidrug resistance-related protein (MRP) but not P-glycoprotein. The MCF-7/VP cells were provided by Drs. Schneider and Cowan (E. Schneider et al., *Cancer Res.* 54:152–158 (1994). The effects of Compound A on cell growth were characterized using the sulforhodamine binding assay (P. Skehan et al., *J. Natl. Cancer Inst.* 82:1107–1112 (1990)) as described in C. D. Smith et al., *Oncology Res.* 6:211–218 (1994) and C. D. Smith et al., *Mol. Pharm.* 45:241–247 (1995). Cell survival was assayed after 48 hours of treatment and was expressed as the percentage of cells killed.

Figure 3:
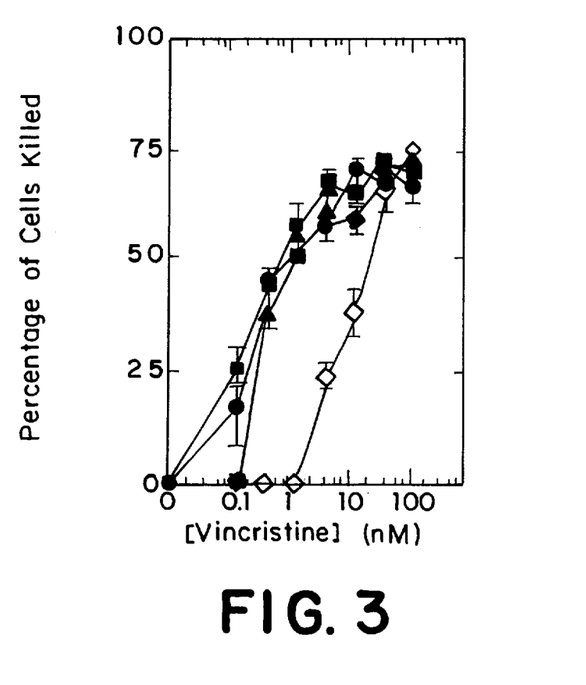
FIG. 3 shows the chemosensitization of MCF-7/VP cells by Compound A. MCF-7/VP cells were treated with the indicated concentrations of vincristine in the presence of ethanol (◊), 20 μM verapamil (■), 5 μM Compound A (●) or 10 μM Compound A (▲).

The results of the chemosensitization tests showing the effect of Compound A on cytotoxicity due to the anticancer drug vincristine in the multiple drug resistant MCF-7/VP cells are given in FIG. 3. Values shown in FIG. 3 represent the mean±standard deviation for triplicate samples in one of three similar experiments.

In comparison with MCF-7 cells, MCF-7/VP cells were 15-fold resistant to the anticancer drug vincristine. Treatment of MCF-7/VP cells with either 5–10 μM Compound A or 20 μM verapamil increased the cytotoxicity of vincristine as shown in FIG. 3. MRP-mediated resistance to vincristine in the MCF-7/VP cells was fully reversed by 10 μM Compound A. Similarly, Compound A also potentiated the cytotoxicities of etoposide and doxorubicin in MCF-7/VP cells, but did not modulate responses to cisplatin in MCF-7/VP cells.

This experiment demonstrated that Compound A fully reverses MRP-mediated resistance to the anticancer drug vincristine in the MCF-7/VP cell line. Compound A also increased the chemosensitivity of MCF-7/VP cells to etoposide and doxorubicin.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:
1. A compound having the formula:

wherein $R_1$, $R_3$ and $R_5$ are independently selected from the group consisting of —H, OH, —SH, —NR'R", a straight or branched, substituted or unsubstituted alkyl group, having 1–6 carbon atoms, a cycloalkyl group having 4–6 carbon atoms or a cycloalkylalkyl group having 4–10 carbon atoms, said $R_1$, $R_3$ and $R_5$ being not all the same, and $R_2$, $R_4$ and $R_6$ are independently selected from the group consisting of —H, —OH, —SH, —NR'R", a straight or branched, substituted or unsubstituted alkyl group having 1–6 carbon atoms, a cycloalkyl group having 4–6 carbon atoms or an cycloalkylalkyl group having 4–10 carbon atoms, at least one of $R_2$, $R_4$ and $R_6$ being other than —H, said alkyl group substituents in $R_1$, $R_2$, $R_3$, $R_4$, $R_5$ and $R_6$ being selected from the group consisting of —OH, —SH, —NR'R", halogen, -O-alkyl having 1–6 carbon atoms or -S-alkyl having 1–6 carbon atoms, and said R' and R" radicals being selected from the group consisting of —H and alkyl having 1–6 carbon atoms, $X_1$, $X_2$ and $X_3$ are independently selected from the group consisting of oxygen and sulfur, the amino acid residues represented by $R_1$, $R_3$ and $R_5$ having the D configuration, and the stereoisomers and pharmaceutically acceptable salts thereof.

2. A compound as claimed in claim 1, wherein $X_1$ and $X_2$ represent S, $X_3$ represents O and $R_1$, $R_2$, $R_3$, $R_4$, $R_5$, $R_6$ are selected from the group consisting of H and a straight or branched alkyl having 1–4 carbon atoms.

3. A compound as claimed in claim 1, wherein $R_1$ represents isopropyl, $R_2$ and $R_4$ represent hydrogen, $R_3$, $R_5$ and $R_6$ represent methyl, $X_1$ and $X_2$ represent S, and $X_3$ represents O.

* * * * *